United States Patent [19]

Ohtake

[11] Patent Number: 5,483,967
[45] Date of Patent: Jan. 16, 1996

[54] BIOELECTRIC SIGNAL RECORDING DEVICE

[76] Inventor: Tutomu Ohtake, 3-60-1 Yotsuya-cho, Toyokawa-shi, Aichi-ken, Japan

[21] Appl. No.: 160,722

[22] Filed: Dec. 2, 1993

[30] Foreign Application Priority Data

Feb. 23, 1993 [JP] Japan .................................. 5-059516

[51] Int. Cl.⁶ ...................................................... A61B 5/04
[52] U.S. Cl. ........................ 128/695 R; 128/903; 607/60
[58] Field of Search ..................................... 128/640, 695, 128/696, 699, 700, 702, 703, 710, 903, 904, 639, 641, 644; 607/60, 148, 152, 153

[56] References Cited

U.S. PATENT DOCUMENTS

| 3,212,496 | 10/1965 | Preston | 128/903 |
|---|---|---|---|
| 3,851,320 | 11/1974 | Dahl | 128/903 |
| 3,943,918 | 3/1976 | Lewis | 128/903 |
| 3,949,388 | 4/1976 | Fuller | 128/903 |
| 4,763,660 | 8/1988 | Kroll et al. | 128/640 |
| 4,791,933 | 12/1988 | Asai et al. | 128/903 |
| 4,809,705 | 3/1989 | Ascher | 128/710 |
| 4,858,617 | 8/1989 | Sanders | 128/710 |
| 4,883,457 | 11/1989 | Sibalis | 607/152 |
| 5,257,631 | 11/1993 | Wilk | 128/710 |
| 5,310,404 | 5/1994 | Gyory et al. | 607/153 |

FOREIGN PATENT DOCUMENTS

| 8809643 | 12/1988 | WIPO | 128/640 |
|---|---|---|---|
| 9319667 | 10/1993 | WIPO | 128/640 |

Primary Examiner—William E. Kamm
Assistant Examiner—Marianne Parker
Attorney, Agent, or Firm—William A. Drucker

[57] ABSTRACT

A device capable of recording a bioelectrical signal under the normal living conditions of a living body is arranged so that an extremely real record can be obtained not only during a walk, a meal or a sleep of the living body but also even during bathing. A base member having flexibility which permits it to follow the motion of the living body is provided with electrodes for picking up electrical signals of the living body and a recording element for recording the picked-up electrical signals. If the base member is stuck on the living body, the electrodes pick up the electrical signals of the living body and the picked-up electrical signals are recorded in the recording element. When the base member is stuck on the living body, the base member watertightly covers the electrodes. Accordingly, even if the living body is surrounded by water, the electrodes can pick up the electrical signals of the living body without touching the water.

6 Claims, 1 Drawing Sheet

BIOELECTRIC SIGNAL RECORDING DEVICE

BACKGROUND OF THE INVENTION

1. Field of the Invention

The present invention relates to a bioelectrical signal recording device for recording an electrical signal from a living body, such as a electrocardiographic signal, an electroencephalographic signal or an electromyographic signal, and, more particularly, to a bioelectrical signal recording device which can move integrally with the living body and can record the electrical signal under the normal living conditions of the living body.

2. Description of the Prior Art

A portable electrocardiograph which is one example of this kind of bioelectrical signal recording device is arranged in such a manner that its electrodes for taking out electrocardiographic signals are attached to corresponding measuring points on the body and a recorder is fixed to the waist by a belt, and the electrocardiographic signals taken out by the respective electrodes are recorded in the recorder. With such a bioelectrical signal recording device, it is possible to record the electrical signals under normal living conditions, for example, during an outdoor walk, an indoor meal or sleep. This record is greatly useful in diagnosing the disease of a patient.

However, this conventional bioelectrical signal recording device has the problem that since it must be removed from the body during bathing, it is impossible to record electrical signals produced during bathing which causes great variations in the states of activities of the internal organs of the body, with the result that a partially insufficient diagnosis is made.

SUMMARY OF THE INVENTION

The present invention has been made to solve the above-described problem (technical subject) of the prior art, and an object of the present invention is to provide a bioelectrical signal recording device capable of providing extremely real records not only during the above-described walk, meal or sleep but also even during bathing so that the exactness of the aforesaid diagnosis can be improved.

To achieve the above object, the bioelectrical signal recording device according to the present invention includes a sheet-like base member having a flexibility which permits the base member to follow a motion of a living body and one face formed as a sticking face which serves to stick the base member on the living body, one or a plurality of electrodes provided on said face of the base member for picking up an electrical signal of the living body, and a recording element provided on the base member for recording the electrical signal picked up by the one or plurality of electrodes. The base member has a sufficient size to watertightly cover the one or plurality of electrodes.

When the bioelectrical signal recording device according to the present invention is stuck on the living body, the respective electrodes pick up the electrical signals of the living body and the picked-up electrical signals are recorded in the recording element. When the bioelectrical signal recording device is stuck on the living body, the base member watertightly covers the electrodes. Accordingly, even if the living body is surrounded by water, the electrodes can pick up the electrical signals of the living body without touching the water.

Since the recording device according to the present invention includes the base member of sheet-like shape which is provided with the electrodes for picking up the electrical signals of the living body and the recording element for recording the picked-up electrical signals, merely by sticking the recording device on the body, it is possible to record the bioelectrical signals under normal living conditions, for example, during an outdoor walk, an indoor meal or sleep.

In the above-described recording, even during bathing which causes great variations in the states of activities of the internal organs of the body, it is possible to record the aforesaid electrical signals with the base member preventing water from adhering to the electrodes. Accordingly, it is possible to provide extremely real records even during the interval that the great variations occur in the states of activities of the internal organs of the body, and the obtained records are greatly useful for diagnosis.

Further, in the present invention, if the arrangement of the plurality of electrodes is selected to correspond to the arrangement of a plurality of predetermined measuring points on the living body, the plurality of electrodes can be made to adhere to the respective predetermined measuring points on the body merely by sticking the living-body electrical signal recording device as one unit on the body at a predetermined location thereof. Accordingly, even a beginner can obtain correct records from correct measuring points by a simple sticking operation.

Other objects and advantages of the invention will become apparent during the following discussion of the accompanying drawings.

DESCRIPTION OF THE PREFERRED EMBODIMENTS

Figure 1:
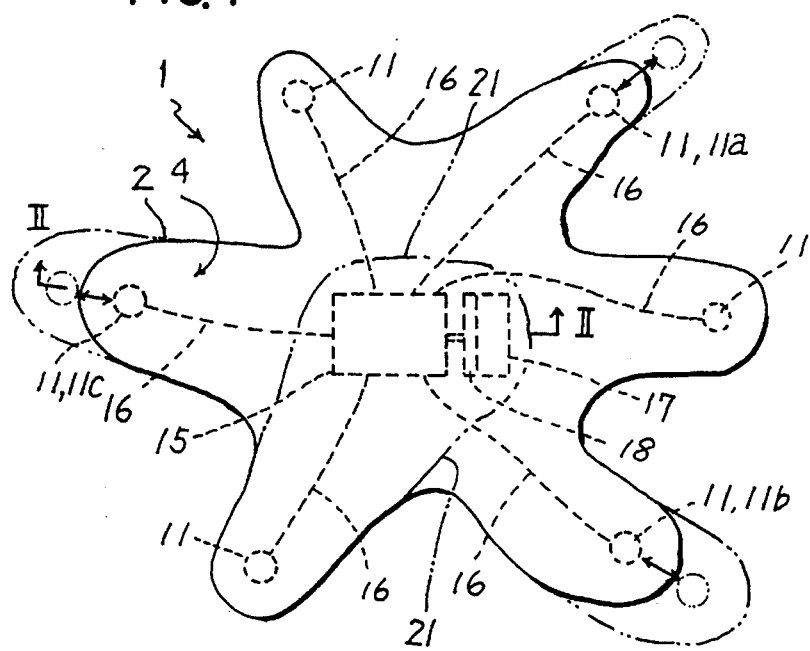
FIG. 1 is a diagrammatic top plan view showing one embodiment of bioelectrical signal recording device according to the present invention.
Figure 2:
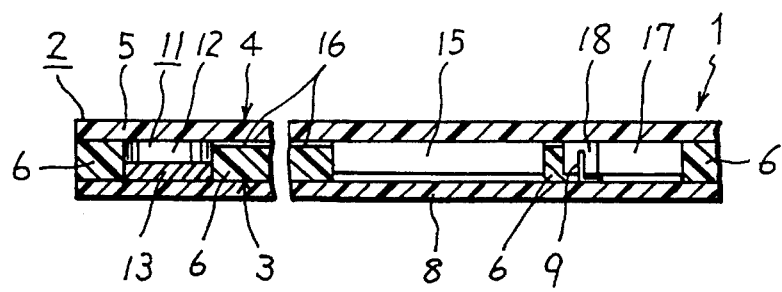
FIG. 2 is a partially omitted, enlarged cross-sectional view taken along line II—II of FIG. 1.

Embodiments of the present invention will be described below with reference to the accompanying drawings. FIGS. 1 and 2 schematically show the arrangement of one example of a bioelectrical signal recording device 1, and the shown example is an electrocardiographic recording device which is arranged to record an electrocardiographic signal as one example of the electrical signals of the living body. A base member 2 of sheet-like shape has a flexibility which permits the base member 2 to follow the motion of the living body. The base member 2 has an internal face 3 and an external face 4, and the internal face 3 is formed as a sticking face which serves to stick the base member 2 on the living body. To watertightly cover a plurality of electrodes which will be described later, the base member 2 of sheet-like shape is formed to be a size larger than a predetermined arrangement pattern according to which the plurality of electrodes are arranged. Further, the size of the base member 2 is selected to contain a portion for holding a recording element, a battery, a switch and the like. The thickness of the base member 2 is preferably small, for example, approximately 2 mm, so that the fit between the base member 2 and the skin can be improved. The structure of the base member 2 will be described below. The base member 2 includes a base 5, and, for example, a synthetic resin sheet having a waterproofing property is used as the base 5 to prevent the electrodes, the recording elements, the battery and the like to be described later respectively from being exposed to water. As another example, it is also possible to utilize rubber, waterproofed paper or cloth, or the like. The base 5 is provided with a shielding property for shielding out electrical noise which tends to penetrate toward the electrodes from the side opposite to the sticking face. For example, the base 5 includes a built-in conductive film for electrical shielding. If another means for shielding out electrical noise is adopted or if no electrical shielding is needed, material having no shielding property may be used for the base 5. Adhesive 6 serves to give an adhesion relative to the living body to the internal face 3 of the base member 2, and an adhesive which can retain a sufficient adhesion strength even if it is wetted is used; a viscous material having an insulation property for electrically insulating the electrodes is utilized. A member 8 serves to prevent the internal face 3 from accidentally adhering to a subject other than the living body or to protect the internal face 3 from dust. The shown example is a removable piece which can be easily removed from the internal face 3. The removable piece 8 has a size which covers the whole of the internal face 3. A conduction preventing member 9 is made from a small piece for the sake of miniaturization, and is attached to the removable piece 8 so that it can be removed integrally with the removable piece 8.

The electrodes for picking up electrical signals of the living body are each indicated by reference numeral 11, and are provided on the same side as the internal face 8 of the base member 2. The arrangement of the plurality of electrodes 11 shown in FIG. 1 is selected to correspond to the arrangement of a plurality of predetermined measuring points on the living body. Each of the electrodes 11 has a structure similar to those of well-known electrodes, and includes a disk-shaped electrode body 12 made of a metal material and a conductive paste 13. A recording element 15 is provided for recording electrical signals picked up by the electrodes 11. As the recording element 15, a thin and small element, for example, an integrated circuit, is used to suppress the sensation of foreign matter touching the skin, which is often experienced by a user during the use of the recording device 1. The recording element 15 is provided with an output terminal through which to take out recorded electrical signals. The recording element 15 is provided on the internal-face side of the base 5 so that waterproofing and electrical-noise shielding can be achieved by the base 5. However, if the recording element 15 itself has a waterproofing property and an electrical-noise shielding property or if no such property is needed, the recording element 15 may be provided on the external-face side of the base 5. Electrical connection lines 16 are provided for electrical connection between the respective electrodes 11 and the recording element 15. A battery 17 is used as a power source for causing the recording element 15 to operate. For a reason similar to that described above in connection with the recording element 15, a thin battery is preferably used as the battery 17. For example, a thin battery called paper battery is preferably used. A switch member 18 is provided for enabling and disabling electrical conduction from the battery 17 to the recording element 15. If the conduction preventing member 9 is attached to the switch member 18, the switch member 18 is held in its nonconducting state, while if the conduction preventing member 9 is removed, the switch member 18 is placed in its conducting state.

The following is a description of the way and state in which the recording device 1 having the above-described arrangement is used. In use, the removable piece 8 is first removed to expose the internal face 3. By removing the removable piece 8, the conduction preventing member 9 is removed from the switch member 18 so that the switch member 18 enables electrical conduction from the battery 17 to the recording element 15 and the recording element 15 starts its recording operation. The recording device 1 placed in this state is stuck on the body by means of the adhesive 6 with the internal face 3 facing the skin. This sticking is performed in such a manner that the internal face 3 adheres to the skin in the state of completely surrounding each of the plurality of electrodes 11. The sticking position is selected so that the recording device 1 is positioned at a predetermined location on the body. Since the electrodes 11 constitute the predetermined arrangement pattern as described above, the plurality of electrodes 11 can be made to adhere to the predetermined measuring points on the body merely by sticking the recording device 1 as one unit on the body at the predetermined location thereof in the above-described manner. Accordingly, even a beginner can obtain correct records from correct measuring points by a simple sticking operation.

The user may perform activities similar to those which he/she has performed in everyday life, with the recording device 1 stuck in the above-described state. During this process, electrocardiographic signals are picked up at the individual measuring points by the respective electrodes 11 at all times, and the picked-up electrocardiographic signals are recorded in the recording element 15 one after another. While the recording device 1 is attached in the above-described state, the user can, of course, walk or run and may also bathe or swim. During bathing or swimming, the base member 2 which has tightly adhered to the skin covers the electrodes 11 to prevent water from touching the electrodes 11. Accordingly, the operation of the electrodes 11 to pick up the electrocardiographic signals is not at all adversely influenced, and the aforesaid recording is continued without abnormality.

When an electrocardiographic record for a predetermined interval of time is obtained in the above-described manner, the recording device 1 is removed from the body. The record in the recording element 15 is read into and analyzed by a computer or other equipment, and the analysis result is utilized in diagnosis.

If a bioelectrical signal is to be picked up at one location on the living body, the above-described recording device may have only the arrangement shown in the portion defined by a chain double-dashed line 21 in FIG. 1, that is, only one electrode 11. In a case where the above-described recording device is a device for recording electroencephalographic signals and if the base member does not have an electrical shielding property, after the recording device has been attached to the head, the user may wear a cap having an electrical shielding property on the recording device so that the adverse influence of electrical noise can be eliminated.

Figure 3A:
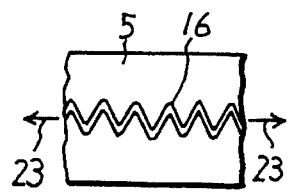
FIGS. 3A and 3B are schematic views showing the state on a sticking-face side of one of connection lines which are expandably and shrinkably provided on a base.
Figure 3B:
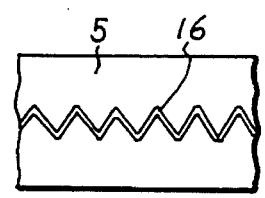

When electrocardiography is to be performed, the aforesaid plurality of electrodes 11 shown in FIG. 1 may be selectively attached in such a manner that an electrode indicated by reference numeral 11a is attached to the skin at the upper end of the sternum, an electrode indicated by reference numeral 11b is attached to the skin at the left-side, fifth intercostal and an electrode indicated by reference numeral 11c is attached to the skin at the right-side, fifth intercostal. However, the distances between the respective attachment points differ from user to user owing to the differences in size between individuals, the differences between the sexes and the like. Particularly, the distances between the attachment points at the right- and left-side, fifth intercostals greatly differ among users (for example, 25 cm to 30 cm). To cope with this problem, the base member 2 may be formed as an expandable member so that the electrodes 11a, 11b and 11c can be displaced as indicated by corresponding arrows. In this case, it is possible to attach the electrodes 11a, 11b and 11c to their respective optimum points even in the case of a user whose distances between the respective attachment points are relatively large or small. To achieve this object, the base 5 may preferably be formed from a material which is expandable and shrinkable, for example, a polyurethane film, and the adhesives 6 may preferably be formed from a material which can expand and shrink according to an expansion or shrinkage of the base 5, for example, a hydrophobicpolymer. Further, the connection lines 16 which extend along the base 5 may preferably be formed expandably and shrinkably. For example, each of the connection lines 16 may be arranged in a zigzag as shown in FIG. 3A so that as the base 5 is expanded, for example, in the directions indicated by arrows 23, the associated connection line 16 expands in the same directions until the state shown in FIG. 3B is reached. The other electrodes 11 may be similarly displaceably arranged so that it is possible to cope with the differences in the distances between the respective attachment points among individuals.

Figure 4:
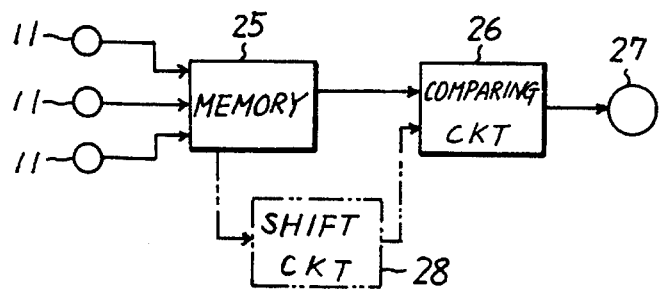
FIG. 4 is a block diagram showing a different example of a recording element.

The aforesaid recording element 15 may preferably be provided with the function of raising an alarm if the electrocardiographic signals picked up by the electrodes 11 show abnormality. To achieve this function, the recording element 15 is made up of a memory 25, a comparing circuit 26 and an alarm element 27 as shown in FIG. 4. In this recording element 15, the memory 25 stores the electrocardiograph signals picked up by the plurality of electrodes 11. The comparing circuit 26 receives the picked-up signals, and causes the alarm element 27 to operate if any of the picked-up signals are deviated from a reference signal. If the recording device provided with the above-described recording element 15 is attached to a patient being examined, the recording device picks up, if the patient develops an apnea state during a sleep, the accompanying abnormality occurring in electrocardiographic signals and can immediately raise an alarm. It is preferable that a standard signal applicable to a multiplicity of persons in common be employed as the reference signal in the comparing circuit 26. Otherwise, a signal appearing during the normal state of the patient being examined may be used as the reference signal, and may be inputted, for example, from the memory 25 to the comparing circuit 26 through a shift circuit 28. This arrangement is preferable because even if there are differences among individual patients, it is possible to raise the aforesaid alarm under conditions best suited to each patient.

As many apparently widely different embodiments of this invention may be made without departing from the spirit and scope thereof, it is to be understood that the invention is not limited to the specific embodiments thereof except as defined in the appended claims.

What is claimed is:

1. A bioelectrical signal recording device comprising:
   (a) a flexible, waterproof, sheet-like base member adherable to a living body and capable of following the motion of said living body, said base member having an adhering face containing an electrically conductive adhesive thereon for adherence to said living body;
   (b) a plurality of electrodes disposed on an interior surface of said base member for receiving electrical signals from said living body;
   (c) a recording element disposed on an interior surface of said base member and having a plurality of connection lines disposed within said base member, each of said connection lines coupled to one of said plurality of electrodes for recording said electrical signals received by said electrodes; and
   (d) a battery disposed within said base member and coupled to said recording element for powering said recording element;
   (e) said base member being of sufficient dimensions to watertightly cover said at least one electrode, said recording element and said battery.

2. The bioelectrical device of claim 1 wherein said base member is an electrical shield for said electrodes for shielding out electrical noise emanating external to said living body and said bioelectrical device.

3. The bioelectrical device of claim 1 wherein said adhering face of said base member includes a removable member for protecting said adhering face.

4. The bioelectrical device of claim 3 further including a normally open switch coupled between said battery and said recording element for enabling and disabling connection between said battery and said recording element and means coupled to said removable member and responsive to removal of said removable member to close said switch and enable electrical connection between said battery and said recording element.

5. The bioelectrical device of claim 1 wherein said electrodes are arranged on said base member to correspond to the arrangement of a plurality of predetermined measuring point on said living body.

6. The bioelectrical device of claim 5 wherein said base member is an electrical shield for said electrodes for shielding out electrical noise emanating external to said living body and said bioelectrical device.

* * * * *